(12) United States Patent
Kwak et al.

(10) Patent No.: US 11,819,327 B1
(45) Date of Patent: Nov. 21, 2023

(54) METHOD AND APPARATUS FOR PROVIDING A MULTI-DIMENSIONAL AUDIOGRAM

(71) Applicant: Sound Vaccine, Inc., Daejeon (KR)

(72) Inventors: Sangyeop Kwak, Seoul (KR); Eunyee Kwak, Seoul (KR); Woojin Doo, Goyang-si (KR); Daehee Lee, Seoul (KR); Sungshin Jang, Hwaseong-si (KR); Songhwa Kim, Daegu (KR); Sunghwan Kim, Seoul (KR)

(73) Assignee: SOUND VACCINE, INC., Daejeon (KR)

( * ) Notice: Subject to any disclaimer, the term of this patent is extended or adjusted under 35 U.S.C. 154(b) by 0 days.

(21) Appl. No.: 18/147,086

(22) Filed: Dec. 28, 2022

Related U.S. Application Data

(63) Continuation of application No. PCT/KR2022/095152, filed on Nov. 28, 2022.

(30) Foreign Application Priority Data

Jun. 21, 2022 (KR) ........................ 10-2022-0075643

(51) Int. Cl.
A61B 5/12 (2006.01)
(52) U.S. Cl.
CPC .................................... *A61B 5/121* (2013.01)

(58) Field of Classification Search
CPC ............ A61B 5/12–128; A61B 5/7228; A61B 5/7235; G01K 15/02; H04R 3/04; H04R 2430/03; H04S 7/30
See application file for complete search history.

(56) References Cited

U.S. PATENT DOCUMENTS

2021/0152933 A1* 5/2021 Boley ................. G06F 3/04847

FOREIGN PATENT DOCUMENTS

| WO | WO-2004071280 A2 * | 8/2004 | ............. A61B 5/121 |
| WO | WO-2005125277 A2 * | 12/2005 | ............. A61B 5/121 |
| WO | WO-2007112737 A1 * | 10/2007 | ............. A61B 5/123 |
| WO | WO-2020034010 A1 * | 2/2020 | ............. A61B 5/125 |

* cited by examiner

*Primary Examiner* — Matthew Kremer

(57) ABSTRACT

A multi-dimensional audiogram providing apparatus includes a processor; and a memory connected to the processor, and the memory stores program instructions that, when executed, cause the processor to output a pure tone audiogram related to a hearing threshold for a subject measured in N frequency on a first surface of a polyhedron; to define a plurality of harmonic templates by rearranging the N frequency bands into a frequency set including a plurality of element frequencies; to calculate a standard deviation of hearing thresholds of a plurality of element frequencies to calculate a harmonic template instability degree; to output the calculated harmonic template instability degree on a second surface of the polyhedron; to calculate an average of the hearing thresholds of the plurality of element frequencies to calculate a harmonic template hearing; and to output the calculated harmonic template hearing on a third surface of the polyhedron.

11 Claims, 11 Drawing Sheets

FIG. 2

| 349 | 587 | 988 | 1661 | 2794 | 4699 | 7902 |
| --- | --- | --- | --- | --- | --- | --- |
| 370 | 622 | 1047 | 1760 | 2960 | 4978 | 8372 |
| 392 | 659 | 1109 | 1865 | 3136 | 5274 | 8870 |
| 415 | 698 | 1175 | 1976 | 3322 | 5588 | 9397 |
| 440 | 740 | 1245 | 2093 | 3520 | 5920 | 9956 |
| 466 | 784 | 1319 | 2217 | 3729 | 6272 | 10548 |
| 494 | 831 | 1397 | 2349 | 3951 | 6645 | 11175 |
| 523 | 880 | 1480 | 2489 | 4186 | 7040 | 11840 |
| 554 | 932 | 1568 | 2637 | 4435 | 7459 | |

METHOD AND APPARATUS FOR PROVIDING A MULTI-DIMENSIONAL AUDIOGRAM

CROSS-REFERENCE TO RELATED APPLICATIONS

This application is a continuation of pending PCT International Application No. PCT/KR2022/095152, which was filed on Nov. 28, 2022, and which claims priority to Korean Patent Application No. 10-2022-0075643 filed with the Korean Intellectual Property Office on Jun. 21, 2022. The disclosures of the above patent applications are incorporated herein by reference in their entirety.

TECHNICAL FIELD

The present disclosure relates to a method and apparatus for providing a multi-dimensional audiogram, and more particularly, to a method and apparatus for defining human hearing at the central nervous system auditory neuron level and representing the defined hearing in a three-dimensional space or a multi-dimensional space.

BACKGROUND ART

Sound transmission is a process by which mechanical energy is converted into electrical energy.

Sound entering through the ear canal vibrates the eardrum and opens the ion channels of hair cells located in the basilar membrane of the cochlea to generate action potentials. The generated action potential moves along the auditory nerve pathway, integrates auditory information in the temporal lobe auditory cortex, and transmits sound.

The harmonic template of the temporal lobe auditory cortex is an auditory neuron (AN) tissue with selectivity for harmonic structures. The harmonic template is a mechanism for biological sound extraction and integration of auditory information in the brain, which analyzes music and complex speech sounds.

There is a pure tone audiogram proposed by ISO 8253 as a representative method of representing human auditory ability to detect sound, that is, hearing.

The ISO 8253-based pure tone audiogram defines and represents human hearing on a two-dimensional plane based on a frequency (X) axis and an intensity (Y) axis. The pure tone audiograms represented in this two-dimensional manner have limitations in providing accurate hearing information at the AN level.

As one such example, it is difficult to represent the anomaly level of firing patterns within (between) harmonic template AN groups of the temporal lobe auditory cortex on a two-dimensional pure tone audiogram.

The anomaly level of firing patterns within (between) a specific harmonic template is an important factor in determining a volume of sensorineural tinnitus and a pitch strength of vowels and musical tones. In the ISO 8253-based pure tone audiogram, which has already standardized the X-axis and Y-axis as a frequency index and an intensity index, respectively, it is difficult to additionally represent new audiometric index such as the anomaly level of firing pattern.

DISCLOSURE

Technical Problem

To solve the above problems of the prior art, the present disclosure is to propose a method and apparatus for providing a multi-dimensional audiogram that can easily grasp not only hearing against pure tones, but also hearing against complex sounds that recognize vowels of speech sounds and musical sounds.

Technical Solution

To achieve the above object, according to an embodiment of the present disclosure, there is provided a multi-dimensional audiogram providing apparatus including a processor; and a memory connected to the processor, wherein the memory stores program instructions that, when executed, cause the processor to output a pure tone audiogram related to a hearing threshold for a subject measured in N frequency bands (wherein, N is a natural number of 15 or more) on a first surface of a polyhedron; to define a plurality of harmonic templates by rearranging the N frequency bands into a frequency set including a plurality of element frequencies having an integer ratio relationship; to calculate a standard deviation of hearing thresholds of a plurality of element frequencies in each of the plurality of harmonic templates to calculate a harmonic template instability degree; to output the calculated harmonic template instability degree on a second surface of the polyhedron; to calculate an average of the hearing thresholds of the plurality of element frequencies in each of the plurality of harmonic templates to calculate a harmonic template hearing; and to output the calculated harmonic template hearing on a third surface of the polyhedron.

The frequency set may include a fundamental frequency f0 and a frequency kf0 (wherein, k is a natural number of 2 or more) corresponding to an integer multiple of the fundamental frequency.

An X-axis of the first surface may be defined as frequency band Hz and a Y-axis of the first surface may be defined as intensity dBHL, the second surface may be defined as a Z-axis plane of the first surface, a horizontal axis of the second surface may be defined as the fundamental frequency of each of the plurality of harmonic templates, and a vertical axis of the second surface may be defined as a magnitude of the harmonic template instability degree of each of the plurality of harmonic templates, a horizontal axis of the third surface may be defined as the harmonic template hearing dBHL of each of the plurality of harmonic templates, and a vertical axis of the third surface may be defined as a magnitude of the harmonic template instability degree in the harmonic template hearing.

The magnitude of the harmonic template instability degree may be defined as a value of dBzHL corresponding to a representative value of the hearing threshold in the plurality of element frequencies.

The program instructions may output one or more comparative index curves to represent the harmonic template instability degree or a chronic tinnitus intensity in a passive auditory system or an active auditory system on the second surface or the third surface.

The comparative index curves may include a sinusoidal curve to represent the harmonic template instability degree in a direct current/alternating current (DC/AC) passive auditory system or a weak alternating current active auditory system; a Gaussian curve to represent the harmonic template instability degree in a strong alternating current (AC) active auditory system; and a Rayleigh curve to represent the chronic tinnitus intensity in the strong alternating current (AC) active auditory system.

The program instructions may cause the comparison index curve to be output such that a vertex of the comparison index curve is located in a dBzHL area of a preset range on the vertical axis of the second surface, and may cause the comparison index curve to be output such that the vertex of the comparison index curve is located in a dBHL area of a preset range on the horizontal axis of the third surface.

The dBzHL area of the preset range and the dBHL area of the preset range may be determined by hearing thresholds collected from a plurality of chronic tinnitus subjects.

The program instructions, when there are different harmonic templates with the same harmonic template hearing, may cause the average of the harmonic template instability degree in each of the different harmonic templates to be calculated, and may cause the average of the calculated harmonic template instability degree to be represented on the vertical axis of the third surface.

According to another embodiment of the present disclosure, there is provided a multi-dimensional audiogram providing apparatus including a processor; and a memory connected to the processor, wherein the memory stores program instructions that, when executed, cause the processor to output a pure tone audiogram related to a hearing threshold for a subject measured in N frequency bands (wherein, N is a natural number of 15 or more) on a first surface of a polyhedron; to define a plurality of harmonic templates by rearranging the N frequency bands into a frequency set including a plurality of element frequencies having an integer ratio relationship; to calculate a standard deviation or an average of hearing thresholds of a plurality of element frequencies in each of the plurality of harmonic templates; and to output the calculated standard deviation or the average on one or more surfaces or an interior space of a polyhedron adjacent to the first surface.

According to yet another embodiment of the present disclosure, there is provided a multi-dimensional audiogram providing method, which is a method of examining a multi-dimensional audiogram in a apparatus including a processor and a memory, including the steps of outputting a pure tone audiogram related to a hearing threshold for a subject measured in N frequency bands (wherein, N is a natural number of 15 or more) on a first surface of a polyhedron; defining a plurality of harmonic templates by rearranging the N frequency bands into a frequency set including a plurality of element frequencies having an integer ratio relationship, and calculating a standard deviation of hearing thresholds of a plurality of element frequencies in each of the plurality of harmonic templates to calculate a harmonic template instability degree; outputting the calculated harmonic template instability degree to a second surface of the polyhedron; calculating an average of the hearing thresholds of the plurality of element frequencies in each of the plurality of harmonic templates to calculate a harmonic template hearing; and outputting the calculated harmonic template hearing to a third surface of the polyhedron.

According to still another embodiment of the present disclosure, there is provided a computer program stored in a computer readable recording medium to perform the method.

Advantageous Effects

According to the present disclosure, by providing multi-dimensional audiograms, not only 'hearing against pure tone' provided by ISO 8253, but also 'hearing against complex tone' that recognizes vowels of speech sounds and musical tones can be easily grasped, and the severity level of sensorineural tinnitus may be quickly and accurately estimated.

DESCRIPTION OF DRAWINGS

FIG. 2 is a diagram illustrating N frequency bands by way of example.

FIG. 5 is a diagram illustrating a result of rearranging N frequency bands into a frequency set having an integer ratio relationship according to an embodiment.

BEST MODE

Figure 1:
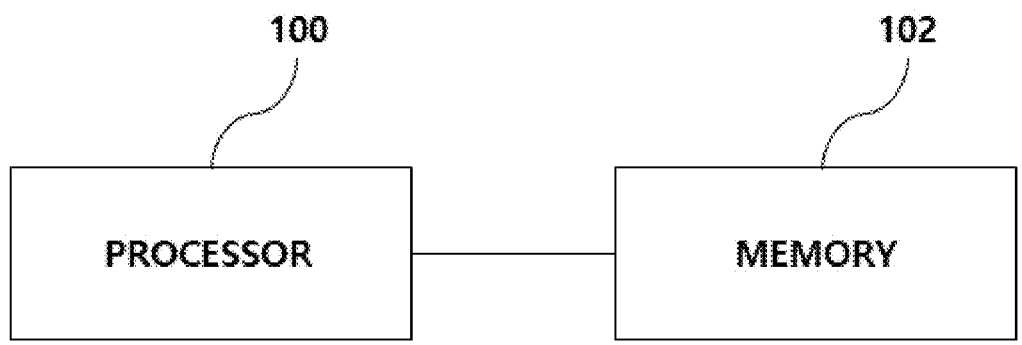
FIG. 1 is a diagram illustrating a configuration of a multi-dimensional audiogram providing apparatus according to a preferred embodiment of the present disclosure.

Since the present disclosure is susceptible to various modifications and alternative forms, specific embodiments thereof are illustrated in the drawings and will be described in detail. However, this is not intended to limit the disclosure to specific embodiments, and should be understood to include all modifications, equivalents, and substitutes within the spirit and technical scope of the disclosure.

The terminology used herein is for the purpose of describing particular embodiments only, and is not intended to limit the present disclosure. Singular expressions include plural expressions unless the context clearly dictates otherwise.
It is to be understood that the terms "comprise" or "have" as used in the present specification are intended to designate the presence of stated features, numbers, steps, operations, components, parts or combinations thereof, but not to preclude the possibility of the presence or addition of one or more other features, numbers, steps, operations, components, parts, or combinations thereof.

In addition, the components of the embodiments described with reference to each drawing are not limitedly applied to the corresponding embodiment, and may be implemented to be included in other embodiments within the scope of maintaining the technical spirit of the present disclosure, and also even if separate description is omitted, it is natural that a plurality of embodiments may be re-implemented as an integrated embodiment.

In addition, in the description with reference to the accompanying drawings, the same or related reference numerals are given to the same components regardless of reference numerals, and overlapping descriptions thereof will be omitted. In describing the present disclosure, when it is determined that the specific description of the known related art may unnecessarily obscure the gist of the present disclosure, the detailed description thereof will be omitted.

FIG. 1 is a diagram illustrating configuration of a multi-dimensional audiogram providing apparatus according to a preferred embodiment of the present disclosure.

As illustrated in FIG. 1, the apparatus according to the present embodiment may include a processor 100 and a memory 102.

The processor 100 may include a central processing unit (CPU) capable of executing a computer program or other virtual machines.

The memory 102 may include a non-volatile storage apparatus such as a non-removable hard drive or a removable storage apparatus. The removable storage apparatus may include a compact flash unit, a USB memory stick, and the like. The memory 102 may also include volatile memory such as various random access memories.

The memory 102 stores program instructions for classifying pathology images based on graph-based image segmentation and semi-supervised learning.

The program instructions according to the present embodiment output pure tone audiograms related to hearing thresholds of a subject measured in N frequency bands (wherein, N is a natural number of 15 or more) on a first surface of a polyhedron.

According to the present embodiment, hearing thresholds for a plurality of frequency bands are measured with high resolution of ⅓ octave or more from 250 Hz to 12,000 Hz, which are the main audible frequencies.

Preferably, the number of N frequency bands may be 62, and FIG. 2 is a diagram illustrating the N frequency bands by way of example.

The hearing thresholds for the N frequency bands are the pure tone audiograms, and are output on the first surface of the polyhedron according to the present embodiment.

Figure 3:
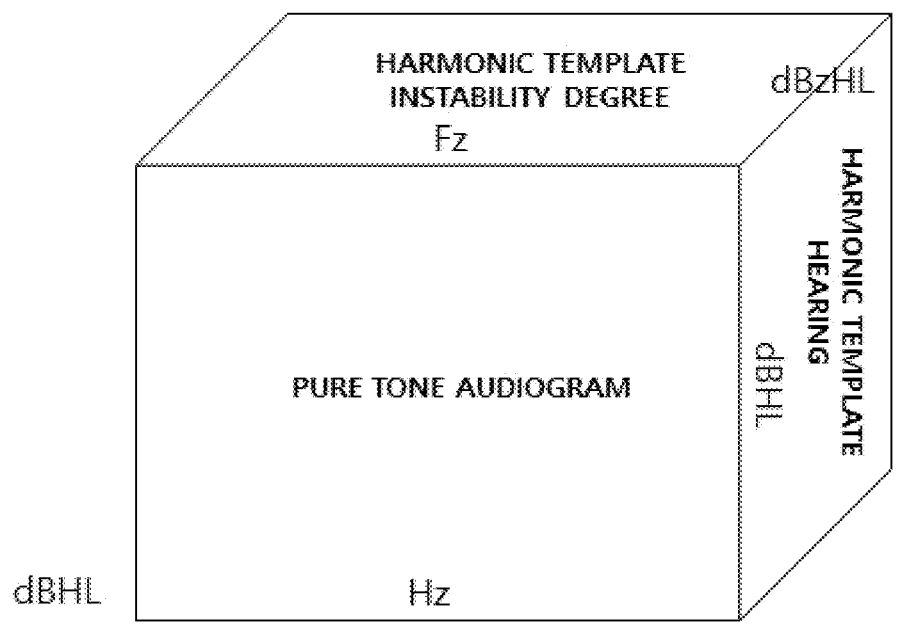
FIGS. 3 and 4 are diagrams illustrating a polyhedron for providing a multi-dimensional audiogram according to an embodiment.
Figure 4:
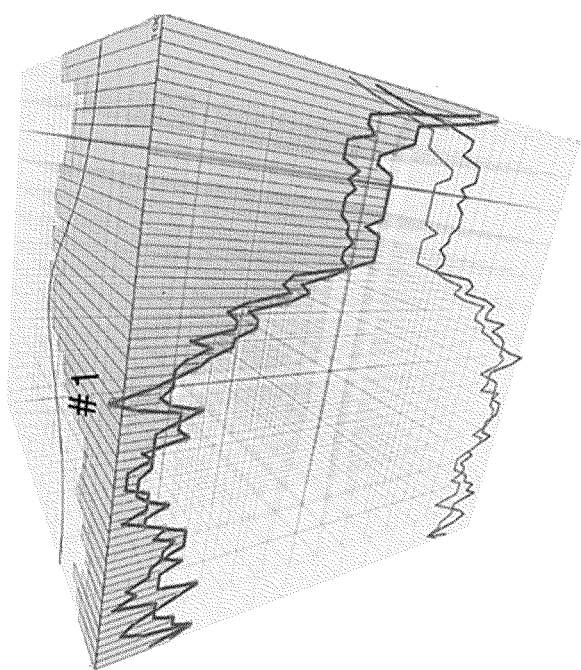
Figure 4:
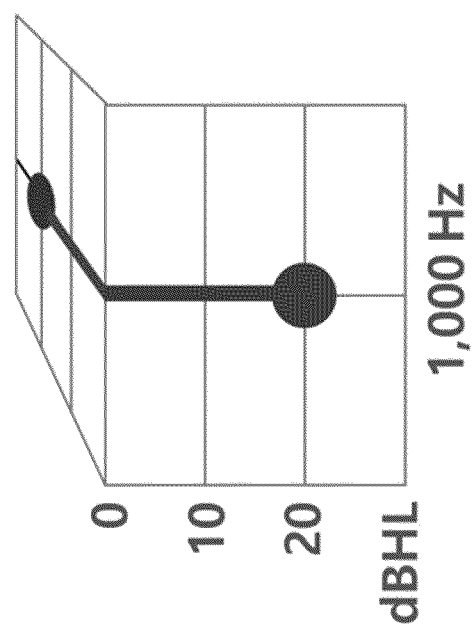

FIGS. 3 and 4 are diagrams illustrating a polyhedron for providing a multi-dimensional audiogram according to the present embodiment.

Referring to FIGS. 3 and 4, in the first surface, an X-axis is defined as a frequency band Hz and a Y-axis is defined as an intensity dBHL.

The first surface illustrates the pure tone audiogram in which the X-axis is defined as the frequency and the Y-axis is defined as the intensity, and FIG. 4 illustrates the hearing threshold for a pure tone having a fundamental frequency of 1,000 Hz on the first surface.

In this embodiment, a polyhedron is provided to represent hearing against complex tones in each frequency band as well as hearing against pure tones at various frequencies.

To provide information such as the anomaly level of firing pattern (or harmonic template instability degree) within (or between) the harmonic template AN group in variety, the apparatus according to the present embodiment defines a plurality of harmonic templates by rearranging the N frequency bands into a frequency set including a plurality of element frequencies having an integer ratio relationship, calculates a standard deviation of hearing thresholds of a plurality of element frequencies in each of the plurality of harmonic templates to calculate a harmonic template instability degree, and outputs the calculated harmonic template instability degree on a second surface.

Figure 5:
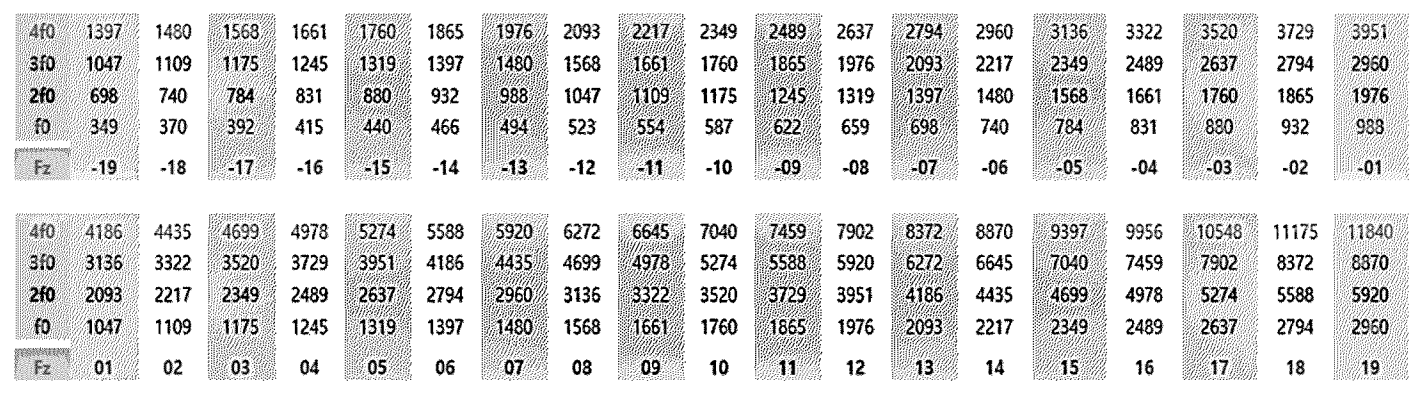

FIG. 5 is a diagram illustrating a result of rearranging N frequency bands into a frequency set having an integer ratio relationship according to an embodiment.

In FIG. 5, the N frequencies are rearranged into a frequency set {f0, 2f0, 3f0, 4f0} with an integer ratio of 1:2:3:4, harmonic templates having a fundamental frequency of 1,000 Hz or more are given as 01(Fz) to 19(Fz) indices, and the harmonic templates below 1,000 Hz are given as −01(Fz) to −19(Fz) indices.

According to the present embodiment, when the hearing thresholds of each of the four elemental frequencies f0, 2f0, 3f0, and 4f0 are t1, t2, t3, and t4 in the frequency set {f0, 2f0, 3f0, 4f0} with 1:2:3:4 integer ratio relationship in each harmonic templates, the standard deviation of t1, t2, t3, and t4 is defined as 'harmonic template instability degree' or 'anomaly level of firing pattern'.

The harmonic template instability degree according to the present embodiment is represented as $\sigma(fn)$ ($\sigma$=sigma).

The apparatus according to the present embodiment calculates the degree of harmonic template instability by calculating the standard deviation of the hearing thresholds of the element frequencies for each harmonic templates, and outputs the degree of harmonic template instability of each harmonic template on the second surface.

As illustrated in FIGS. 3 and 4, the second surface of the polyhedron is defined as the Z-axis surface of the first surface.

Figure 6:
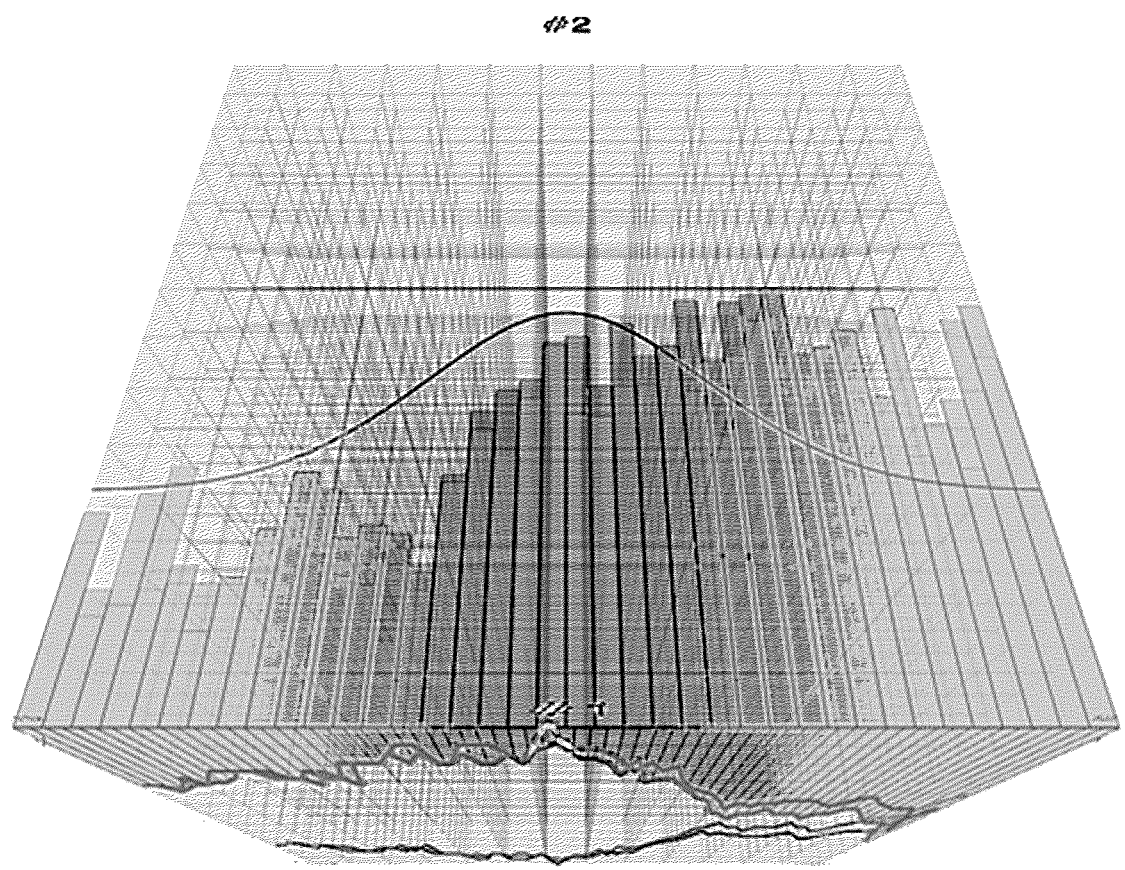
FIG. 6 is a diagram illustrating a second surface of a polyhedron in detail according to an embodiment.

FIG. 6 is a diagram illustrating a second surface of a polyhedron in detail according to the present embodiment.

Referring to FIG. 6, a horizontal axis of the second surface is defined as a fundamental frequency (harmonic template index) of each of the plurality of harmonic templates, and a vertical axis of the second surface is defined as a magnitude of the harmonic template instability degree of each of the plurality of harmonic templates.

When there are 62 frequency bands, the horizontal axis represents the fundamental frequencies of each of the 38 harmonic templates, and the vertical axis represents the magnitude of the harmonic template instability degree defined as the standard deviation of the hearing thresholds of the element frequency in each harmonic template.

In addition, according to the present embodiment, when the hearing thresholds of each of the four elemental frequencies f0, 2f0, 3f0, and 4f0 are t1, t2, t3, and t4 in the frequency set {f0, 2f0, 3f0, 4f0} with 1:2:3:4 integer ratio relationship in each harmonic templates, a value obtained by dividing a sum of (t1+t2+t3+t4) by 4, that is, the average hearing threshold, is defined as 'harmonic template hearing' or 'harmonic template hearing capacity'.

The apparatus according to the present embodiment calculates the average of the hearing thresholds of the element frequencies for each harmonic template to calculate the harmonic template hearing, and outputs the harmonic template hearing of each harmonic template to a third surface.

Figure 7:
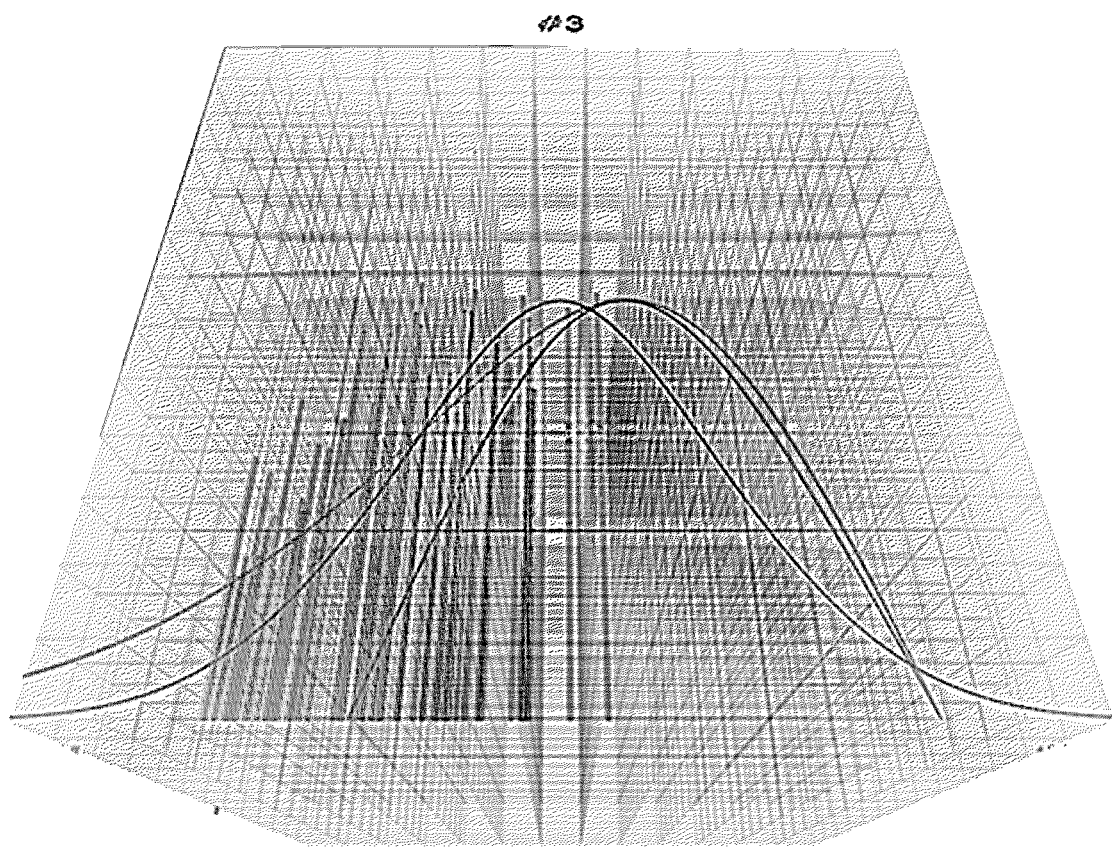
FIG. 7 is a diagram illustrating a third surface of a polyhedron in detail according to an embodiment.

FIG. 7 is a diagram illustrating a third surface of a polyhedron in detail according to the present embodiment.

As illustrated in FIG. 7, a third surface of the polyhedron is defined by the horizontal axis as the harmonic template hearing dBHL of each of the plurality of harmonic templates, and is defined by the vertical axis as the size of the standard deviation of the harmonic template hearing.

In the third surface, the vertical axis may be defined as the firing time distance within (between) the harmonic template AN group as a phase space.

According to the present embodiment, the harmonic template hearing is defined as $\mu(fz)$ ($\mu$=mu), and $\mu(fz)$ values ranging from a minimum of −10 dBHL to a maximum of 120 dBHL may be represented on horizontal axis coordinates of the polyhedral surface.

In this case, the magnitude of the harmonic template instability degree and the magnitude of the harmonic template hearing are defined as a value dBzHL corresponding to a representative value (standard deviation) of the hearing thresholds in a plurality of element frequencies.

According to the present embodiment, by defining the size of a representative value such as the standard deviation of the hearing thresholds in various frequency bands, which is distinguished from dBHL representing the size of the existing hearing threshold, as dBzHL, audiograms for complex tones as well as pure tones are represented.

According to the present embodiment, the second surface and third surface of the polyhedron are defined to include not only the outermost surface but also a surface having a predetermined depth in the inner space.

According to the present embodiment, when there are different harmonic templates having the same harmonic template hearing, the average of the harmonic template instability degree in each of the different harmonic templates is calculated, and the average of the calculated harmonic template instability degree is represented on the vertical axis of the third surface.

Since the horizontal axis of the third surface according to the present embodiment is defined not as a harmonic template index but as a harmonic template hearing, among a plurality of harmonic templates, there may be harmonic templates having the same harmonic template hearing.

In this case, the average of the harmonic template instability degree of the harmonic templates having the same harmonic template hearing is calculated and represented on the vertical axis of the third surface, thereby representing the audiogram for the complex sound in various ways.

According to the present embodiment, as illustrated in FIGS. 6 and 7, by presenting at least one and three or more comparison index curves on the second and third surfaces of the polyhedron, interpretability and understanding of the subject's audiogram may be improved.

Figure 8B:
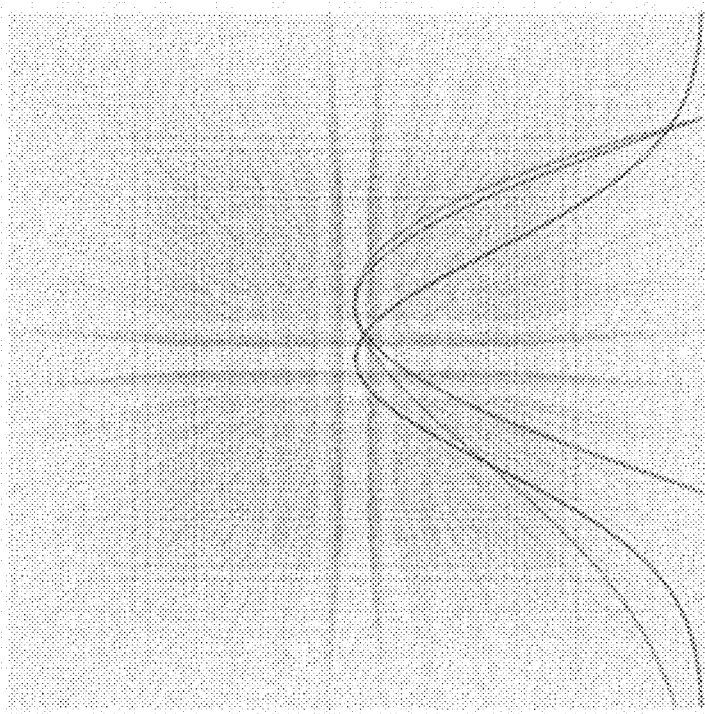
FIGS. 8A and 8B are a diagram illustrating an example of projecting comparison index curves according to an embodiment.
Figure 8A:
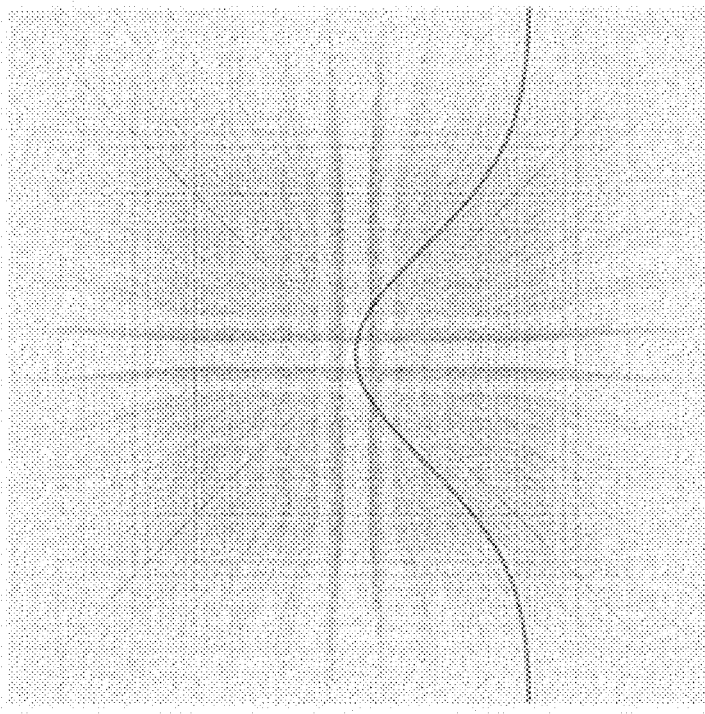

FIGS. 8A and 8B are a diagram illustrating an example of projecting comparison index curves according to the present embodiment.

FIG. 8A is a diagram illustrating a Gaussian curve output on a second surface, and FIG. 8B is a diagram illustrating a sinusoidal curve, a Gaussian curve, and a Rayleigh curve output on a third surface.

According to the present embodiment, a sinusoidal curve or arch curve is used as a first type of comparison index curve.

This represents the stochastic trajectory of the anomaly level of firing pattern within (between) the harmonic template AN group in the direct current/alternating current passive auditory system or the weak alternating current active auditory system.

The passive trajectory $L_p$ of the sinusoid or arch curve is defined by Equation 1 or 2 below, and the corresponding curve is projected onto the surface of the polyhedron or the interior space of the polyhedron to provide a multi-dimensional audiogram.

$$L_F = A\sin\left(\frac{\pi}{90-20}(y-\varphi)\right) \quad \text{[Equation 1]}$$

Herein, A is an amplitude, φ is a phase, and y is the hearing threshold.

$$L_p = A\sin(0.04487990y - 0.89759790) \quad \text{[Equation 2]}$$

According to the present embodiment, the Gaussian curve is used as a second type of the comparison index curve.

This represents the stochastic trajectory of the anomaly level of firing pattern within (between) the harmonic template AN group in the strong alternating current active auditory system.

The direct current/alternating current passive auditory system refers to the electrophysiological characteristics and structure of the auditory nervous system of vertebrate animals (excluding humans) including primates, and the weak AC active auditory system refers to the electrophysiological characteristics and structure of the human auditory nervous system in which large and small irreversible hearing loss has already progressed in a part or wide frequency range within the audible frequency band. The strong alternating current active auditory system refers to the electrophysiological characteristics and structure of the human auditory nervous system in which large and small reversible hearing loss is in progress in a normal hearing human or in a part or wide frequency range within the audible frequency band.

The active trajectory $L_a$ of the Gaussian curve is defined by Equation 3 below, and the corresponding curve is projected onto the surface of the polyhedron or the interior space of the polyhedron.

$$L_a = k \cdot \exp\left(-\frac{(y-55)^2}{2\sigma^2}\right) \quad \text{[Equation 3]}$$

Here, k is a coefficient that determines the peak or plateau of the Gaussian curve, and σ is the standard deviation of the hearing thresholds in a specific hearing unit.

The third type of comparative index curve, the Rayleigh curve represents the stochastic trajectory of chronic tinnitus intensity in the strong AC active auditory system.

The active trajectory $L_c$ of the Rayleigh curve is defined by Equations 4 or 5 below, and the corresponding curve is projected onto the surface of the polyhedron or the interior space of the polyhedron.

$$L_c = f(y) = \frac{y}{\sigma^2}\left(\frac{-y^2}{2\sigma^2}\right) \quad \text{[Equation 4]}$$

$$f_{X,Y}(x,y) = \frac{1}{2\pi\sigma_X\sigma_Y\sqrt{1-\rho^2}}\exp\left(-\frac{1}{2}\left[\frac{1}{1-\rho^2}\left\{\left(\frac{y-\upsilon_Y}{\sigma_Y}\right) - 2\rho\left(\frac{y-\mu_Y}{\sigma_Y}\right)\left(\frac{x-\mu_X}{\sigma_X}\right) + \left(\frac{u-\mu_X}{\sigma_X}\right)^2\right\}\right]\right) \quad \text{[Equation 5]}$$

According to the present embodiment, vertices of the comparison index curve (sinusoidal curve, Gaussian curve, Rayleigh curve, etc.) are output within a preset area on the second surface or the third surface.

Figure 9:
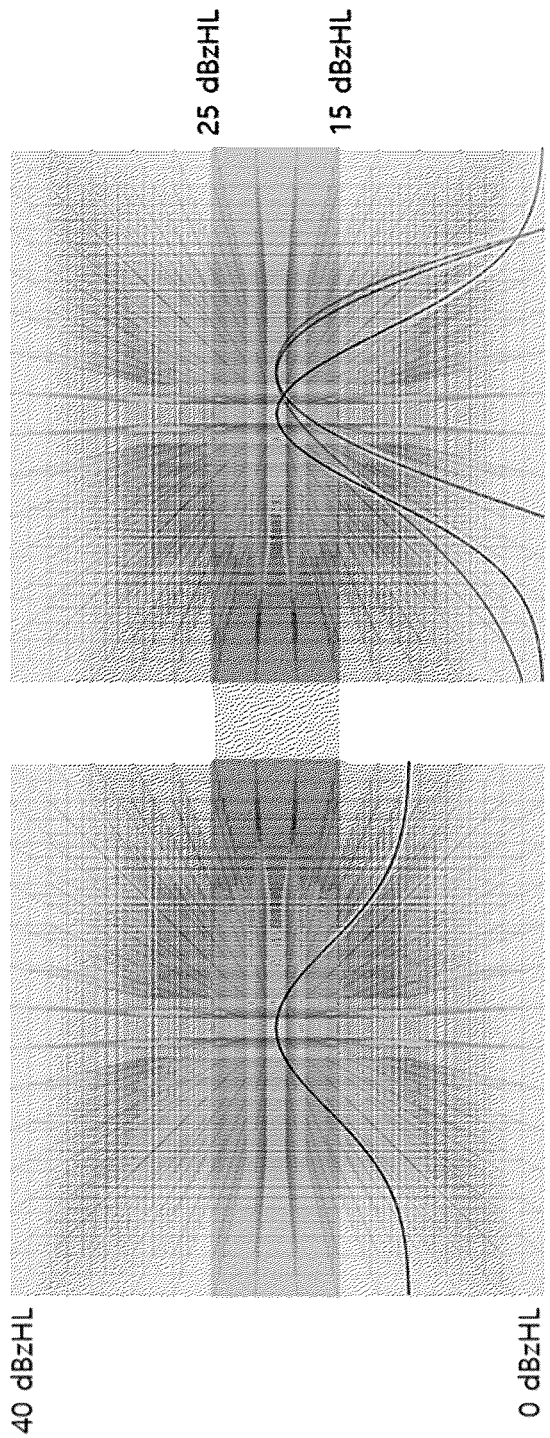
FIG. 9 is a diagram illustrating a state in which a vertex of the comparison index curve is located in an area of 15 to 25 dBzHL on a vertical axis of a second surface.
Figure 10:
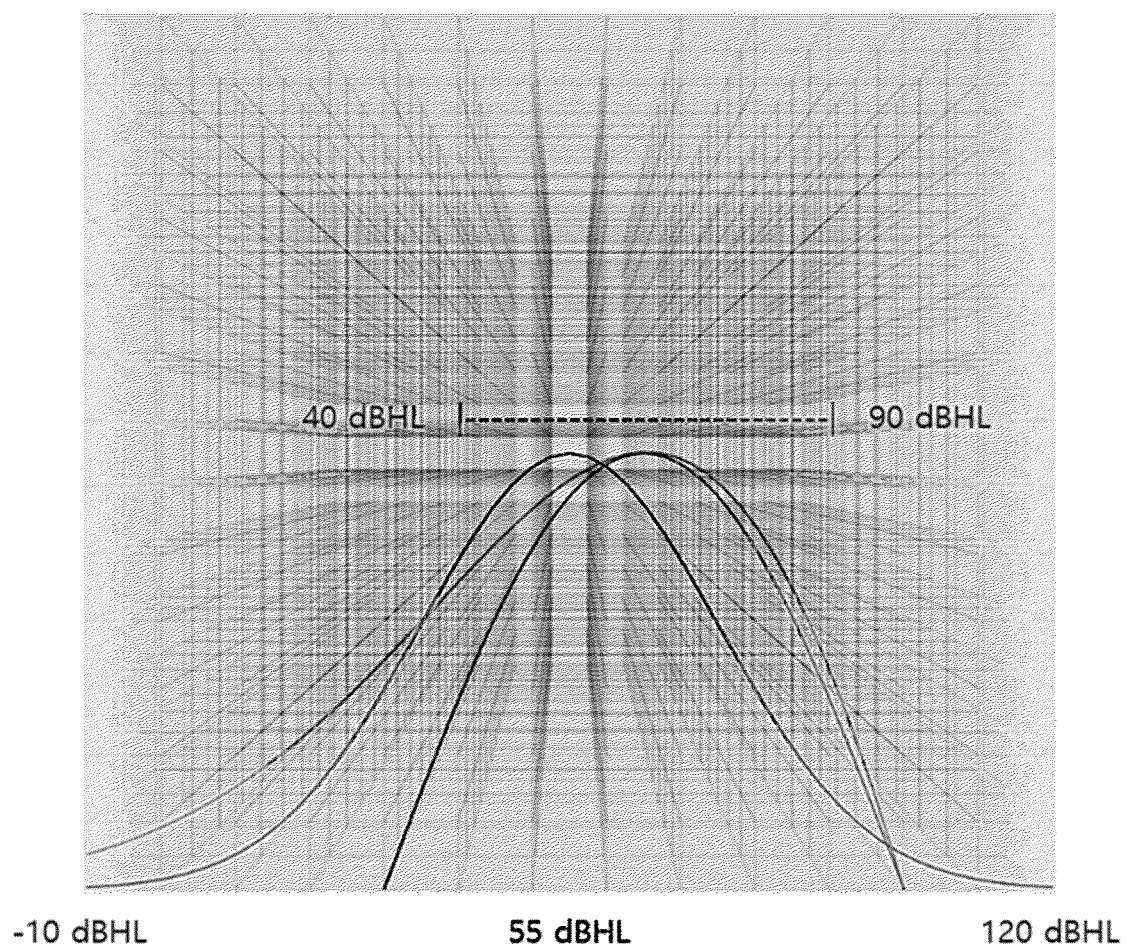
FIG. 10 is a diagram illustrating state in which a vertex of a comparison index curve is located in an area of 40 to 90 dBHL on a horizontal axis of a third surface.

FIG. 9 is a diagram illustrating a state in which the vertex of the comparison index curve is located in the 15 to 25 dBzHL area of the vertical axis of the second surface, and FIG. 10 is a diagram illustrating a state in which the vertex of the comparison index curve is located in the 40 to 90 dBHL area of the horizontal axis of the third surface.

In FIGS. 9 and 10, the area where the vertex of the comparative index curve is located is an index for evaluating the chronic tinnitus, and is determined by considering the average value of a plurality of chronic tinnitus patients. That is, when the comparison index curve of a specific subject is located within the above area, it can be diagnosed as being in the chronic tinnitus state.

Figure 11:
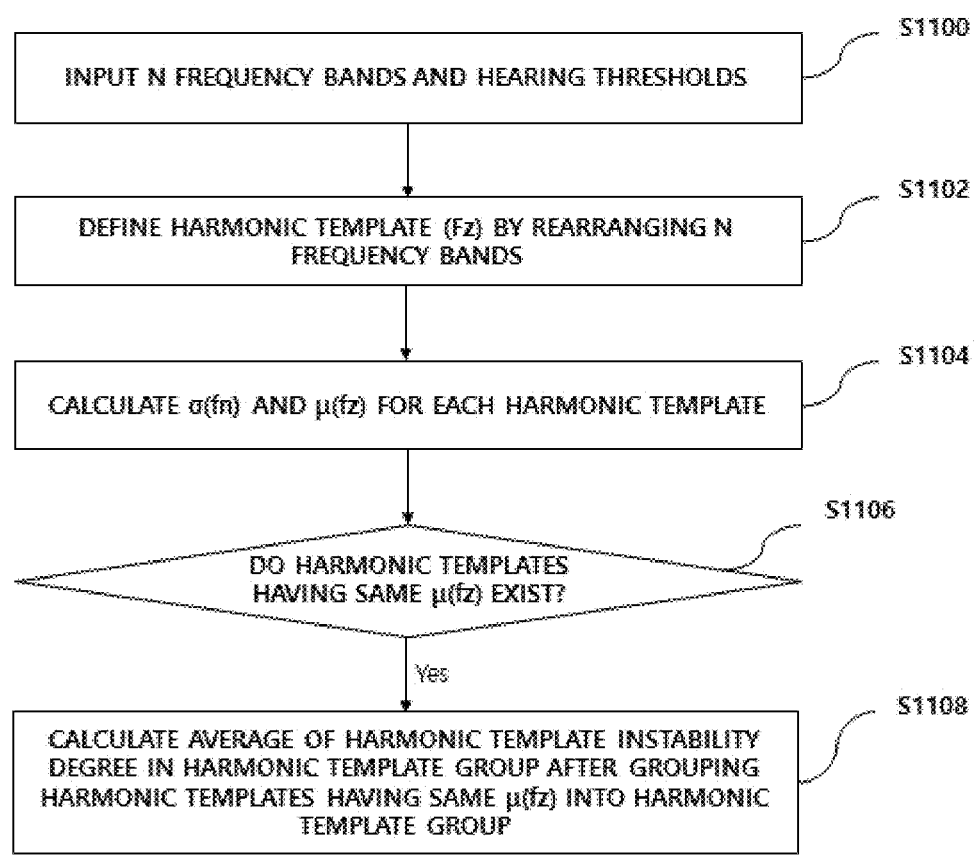
FIG. 11 is a flowchart illustrating a process of representing a harmonic template hearing and a harmonic template instability degree according to an embodiment.

FIG. 11 is a flowchart illustrating a process of representing a harmonic template hearing and a harmonic template instability degree, according to an embodiment.

Referring to FIG. 11, the apparatus according to the present embodiment receives N frequency bands and their hearing thresholds (Step 1100), and rearranges the N frequency bands in an integer multiple relationship to define a harmonic template Fz (Step 1102).

Next, σ(fn) and μ(fz) for each harmonic template are calculated (Step 1104).

The apparatus according to the present embodiment outputs σ(fn) of each harmonic template on the vertical axis of the second surface of the polyhedron and μ(fz) on the horizontal axis of the third surface of the polyhedron.

In addition, in representing the magnitude of σ(fn) at each μ(fz) on the vertical axis of the third surface, it is determined whether there is a harmonic template having the same μ(fz) among the plurality of harmonic templates (Step 1106), and the average of σ(fn) in different harmonic templates having the same μ(fz) is calculated (Step 1108), and the calculated average is output on the vertical axis of the third surface.

The embodiments of the present disclosure described above have been disclosed for illustrative purposes, and those skilled in the art having ordinary knowledge on the present disclosure will be able to make various modifications, changes, and additions within the spirit and scope of the present disclosure, and such modifications, changes, and additions will be considered to fall within the scope of the following claims.

What is claimed is:

1. A display apparatus for displaying a three-dimensional audiogram, comprising:
    a processor; and
    a memory connected to the processor,
    wherein the memory stores program instructions that, when executed, cause the processor to:
    display a pure tone audiogram related to a hearing threshold for a subject measured in fifteen or more frequency bands on a first surface of a polyhedron;
    define a plurality of harmonic templates by rearranging the fifteen or more frequency bands into a frequency set including a plurality of element frequencies having an integer ratio relationship;
    calculate a standard deviation of hearing thresholds of the plurality of element frequencies in each of the plurality of harmonic templates to calculate a harmonic template instability degree for each of the plurality of harmonic templates;
    display the calculated harmonic template instability degree on a second surface of the polyhedron;
    calculate an average of the hearing thresholds of the plurality of element frequencies in each of the plurality of harmonic templates to calculate a harmonic template hearing; and
    display the calculated harmonic template hearing on a third surface of the polyhedron.

2. The apparatus of claim 1, wherein the plurality of element frequencies correspond to an integer multiple of a fundamental frequency.

3. The apparatus of claim 2, wherein an X-axis of the first surface is defined as frequency band Hz and a Y-axis of the first surface is defined as intensity measured in dBHL, the second surface is defined as a Z-axis plane of the first surface, a horizontal axis of the second surface is defined as the fundamental frequency of each of the plurality of harmonic templates, and a vertical axis of the second surface is defined as a magnitude of the harmonic template instability degree of each of the plurality of harmonic templates,
    a horizontal axis of the third surface is defined as the harmonic template hearing measured in dBHL of each of the plurality of harmonic templates, and a vertical axis of the third surface is defined as the magnitude of the harmonic template instability degree in the harmonic template hearing.

4. The apparatus of claim 3, wherein the magnitude of the harmonic template instability degree is defined as a value of dBzHL corresponding to a representative value of the hearing threshold in the plurality of element frequencies.

5. The apparatus of claim 4, wherein the program instructions output one or more comparative index curves to represent the harmonic template instability degree or a chronic tinnitus intensity in a passive auditory system or an active auditory system on the second surface or the third surface.

6. The apparatus of claim wherein the comparative index curves comprise:
    a sinusoidal curve to represent the harmonic template instability degree in a direct current/alternating current (DC/AC) passive auditory system or a weak alternating current active auditory system;
    a Gaussian curve to represent the harmonic template instability degree in a strong alternating current (AC) active auditory system; and
    a Rayleigh curve to represent the chronic tinnitus intensity in the strong alternating current (AC) active auditory system.

7. The apparatus of claim wherein the program instructions:
    cause the comparative index curves to be output such that a vertex of the comparative index curves is located in a dBzHL area of a preset range on the vertical axis of the second surface, and
    cause the comparative index curves to be output such that the vertex of the comparative index curves is located in a dBHL area of a preset range on the horizontal axis of the third surface.

8. The apparatus of claim 7, wherein the dBzHL area of the preset range and the dBHL area of the preset range are determined by hearing thresholds collected from a plurality of chronic tinnitus subjects.

9. The apparatus of claim 3, wherein the program instructions:
    when there are different harmonic templates with the same harmonic template hearing, cause the average of the harmonic template instability degree in each of the different harmonic templates to be calculated, and
    cause the average of the calculated harmonic template instability degree to be represented on the vertical axis of the third surface.

10. A method of examining a three-dimensional audiogram in a display apparatus comprising a processor and a memory, the method comprising the steps of:
    displaying a pure tone audiogram related to a hearing threshold for a subject measured in fifteen or more frequency bands on a first surface of a polyhedron;
    defining a plurality of harmonic templates by rearranging the fifteen or more frequency bands into a frequency set comprising a plurality of element frequencies having an integer ratio relationship, and calculating a standard deviation of hearing thresholds of the plurality of element frequencies in each of the plurality of harmonic templates to calculate a harmonic template instability degree for each of the plurality of harmonic templates;

displaying the calculated harmonic template instability degree to a second surface of the polyhedron;

calculating an average of the hearing thresholds of the plurality of element frequencies in each of the plurality of harmonic templates to calculate a harmonic template hearing; and displaying the calculated harmonic template hearing to a third surface of the polyhedron.

11. A non-transitory computer readable medium comprising executable instructions that, when executed by a processor, perform a method for displaying a three-dimensional audiogram, the method comprising:

displaying a pure tone audiogram related to a hearing threshold for a subject measured in fifteen or more frequency bands on a first surface of a polyhedron;

defining a plurality of harmonic templates by rearranging the fifteen or more frequency bands into a frequency set including a plurality of element frequencies having an integer ratio relationship;

calculating a standard deviation of hearing thresholds of the plurality of element frequencies in each of the plurality of harmonic templates to calculate a harmonic template instability degree for each of the plurality of harmonic templates;

displaying the calculated harmonic template instability degree on a second surface of the polyhedron;

calculating an average of the hearing thresholds of the plurality of element frequencies in each of the plurality of harmonic templates to calculate a harmonic template hearing; and displaying the calculated harmonic template hearing on a third surface of the polyhedron.

* * * * *